(12) United States Patent
Chang et al.

(10) Patent No.: US 9,393,194 B2
(45) Date of Patent: Jul. 19, 2016

(54) BIOCARRIER AND METHOD OF USING THE SAME

(75) Inventors: Yung Chang, Tao-Yuan (TW); Yu-Ju Shih, Tao-Yuan (TW)

(73) Assignee: CHUNG YUAN CHRISTIAN UNIVERSITY, Tao-Yuan (TW)

( * ) Notice: Subject to any disclaimer, the term of this patent is extended or adjusted under 35 U.S.C. 154(b) by 1156 days.

(21) Appl. No.: 12/953,110

(22) Filed: Nov. 23, 2010

(65) Prior Publication Data

US 2012/0128775 A1 May 24, 2012

(51) Int. Cl.
| | |
|---|---|
| *A61K 9/14* | (2006.01) |
| *A61K 31/7052* | (2006.01) |
| *A61K 9/00* | (2006.01) |
| *A61K 47/34* | (2006.01) |
| *A61K 47/48* | (2006.01) |

(52) U.S. Cl.
CPC ............... *A61K 9/0019* (2013.01); *A61K 47/34* (2013.01); *A61K 47/48176* (2013.01)

(58) Field of Classification Search
None
See application file for complete search history.

(56) References Cited

U.S. PATENT DOCUMENTS

| 7,713,541 B1 | 5/2010 | Pacetti et al. | |
|---|---|---|---|
| 8,182,802 B2 * | 5/2012 | Lewis et al. | 424/78.3 |

OTHER PUBLICATIONS

Shih, et al. (Nov. 16, 2010) "Tunable blood compatibility of polysulfobetaine from controllable molecular-weight dependence of zwitterionic nonfouling nature in aqueous solution." Langmuir, 16(22):17286-94.*

* cited by examiner

*Primary Examiner* — Robert M Kelly
(74) *Attorney, Agent, or Firm* — WPAT, PC; Justin King

(57) ABSTRACT

The present invention discloses a biocarrier for delivery of a bioactive substance near/into a target cell, comprising a bioactive substance-loaded core with a first electricity, and one or more block copolymer, each block copolymer comprising a zwitterionic block and an anchoring block with an initial electricity opposite to the first electricity, wherein the anchoring block binds to the core by electrostatic attraction, and the zwitterionic block extends outwardly to increase the biocarrier stability in mammalian blood. Additionally, the present invention also discloses a method of using the biocarrier.

11 Claims, 17 Drawing Sheets

US 9,393,194 B2

BIOCARRIER AND METHOD OF USING THE SAME

CROSS-REFERENCE TO RELATED APPLICATIONS

This application relates to co-pending U.S. application Ser. No. 12/952,913 filed Nov. 23, 2010 and entitled "Surface anti-biomolecule agent"; and relates to U.S. application Ser. No. 12/953,036 filed Nov. 23, 2010 and entitled "Dental care product." The foregoing applications are commonly assigned and the entire contents of all of them are expressly incorporated herein by reference.

BACKGROUND OF THE INVENTION

1. Field of the Invention

The present invention relates to biocarriers and method of using the biocarriers.

2. Description of the Prior Art

To minimize drug degradation and loss, to prevent harmful side-effects and to increase drug bioavailability and the fraction of the drug accumulated in required zone, various drug delivery and drug targeting systems are currently developed or under development. Among drug carriers one can name soluble polymers, microparticles made of insoluble or biodegradable natural and synthetic polymers, microcapsules, cells, cell ghosts, lipoproteins, liposomes, and micelles. Those carriers can be made slowly degradable, stimuli-reactive (for example, pH- or temperature-sensitive), and even targeted (for example, by conjugating them with specific antibodies against certain characteristic components of the area of interest).

Micelles as drug carriers are able to provide a set of unbeatable advantages—they can solubilize poorly soluble drugs and thus increase their bioavailability, they can stay in the mammalian blood (e.g. human blood) long enough providing gradual accumulation in the required area, their size permits them to accumulate in body regions with leaky vasculature, they can be targeted by attachment of a specific ligand to the outer surface, and they can be prepared in large quantities easily and reproducibly. Being in a micellar form, the drug is well protected from possible inactivation under the effect of biological surroundings, it does not provoke undesirable side effects, and its bioavailability is usually increased.

The micelle is structured in such a way that the outer surface of the micelle exposed into the aqueous surrounding consists of components that are hardly reactive towards blood or tissue components. This structural peculiarity allows micelles to stay in the blood (tissues) rather long without being recognized by certain proteins and/or phagocytic cells. This longevity is an extremely important feature of micelles as drug carriers.

In another aspect, gene therapy employs a viral or non-viral vector to carry the therapeutic DNA into the target cells. Viral systems present high delivery and expression efficiencies as they are natural highly evolved DNA carriers. However, safety issues, little DNA carrying capacity, and production problems of the viral vectors have limited their clinical use. Non-viral vectors present advantages including: non-pathogenic, non-immunogenic, larger DNA carrying capacity, and less expensive and easier to produce. However, their transfection and expression efficiencies are relatively low compared to viral systems.

Among the non-viral vectors, the oppositely charged polycation and DNA interact to form a nanometric size polyplex to encapsulate the DNA and protect it before into the cell. The properties of polyplexes are easier to be controlled than other non-viral vectors; however, many polyplexes, such us PEI-PLL, poly(diallyl-dimethyl-ammonium chloride) (DADMAC), diethylaminoethyl-dextran (DEAE-dextran), and poly(vinyl pyridinium bromide)(PVPBr), have been found to be toxic. Moreover, it is found that many polyplexes in contact with red blood cells will highly damage to plasma membranes.

Accordingly, it would be advantageous to develop new biocarriers with high and controllable blood compatibility for medical applications, such as to be employed to construct low cytotoxicity non-viral carriers for efficiently delivering vector DNA to target cells.

SUMMARY OF THE INVENTION

One object of the present invention is to provide a biocarrier for delivery of a bioactive substance near/into a target cell, comprising: a bioactive substance-loaded core with a first electricity; and one or more block copolymer, each block copolymer comprising a zwitterionic block and an anchoring block with an initial electricity opposite to the first electricity, wherein the anchoring block binds to the core by electrostatic attraction, and the zwitterionic block extends outwardly to increase the biocarrier stability in mammalian blood.

Another object of the present invention is to show how block copolymer conformations, such as zwitterionic block lengths, anchoring block lengths, molecular weights, or associations, would influence the correlations between solution properties and blood compatibility.

Still another object of the present invention is to provide a method for delivery of a bioactive substance near/into a target cell, comprising: First, providing a bioactive substance-loaded core with a first electricity, wherein the core is embedded with a bioactive substance; Second, providing one or more block copolymer, each block copolymer comprising a zwitterionic block and an anchoring block with an initial electricity opposite to the first electricity, wherein the anchoring block binds to the core by electrostatic attraction, the zwitterionic block extends outwardly, and a plurality of biocarriers are then self-assembled; Thirdly, injecting the biocarriers into mammalian blood, wherein the biocarriers are circulated to a specific region near the target cell; Finally, performing an adjusting process to adjust the electricity of the anchoring block, so as to break the binding between the anchoring block and the core, the biocarrier is then disassembled to release the bioactive substance.

DESCRIPTION OF THE PREFERRED EMBODIMENT

Reference will now be made in detail to specific embodiments of the invention. Examples of these embodiments are illustrated in accompanying drawings. While the invention will be described in conjunction with these specific embodiments, it will be understood that it is not intended to limit the invention to these embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well-known process operations and components are not been described in detail in order not to unnecessarily obscure the present invention. While drawings are illustrated in details, it is appreciated that the quantity of the disclosed components may be greater or less than that disclosed, except expressly restricting the amount of the components.

The first embodiment of the present invention discloses a biocarrier for delivery of a bioactive substance near/into a target cell, comprising: a bioactive substance-loaded core with a first electricity, wherein the core could be polymer-based; and one or more block copolymer, each block copolymer comprising a zwitterionic block and an anchoring block with an initial electricity opposite to the first electricity, wherein the anchoring block binds to the core by electrostatic attraction, and the zwitterionic block extends outwardly to increase the biocarrier stability in mammalian blood.

The bioactive substance is selected from the group consisting of drug and nucleic acid, and nucleic acid is selected from the group consisting of DNA, DNA encoding a protein, DNA encoding an antisense RNA, DNA encoding a ribozyme, DNA encoding an shRNA, RNA, messenger RNA, siRNA, shRNA, miRNA, antisense RNA, and ribozyme RNA.

Figure 6A:
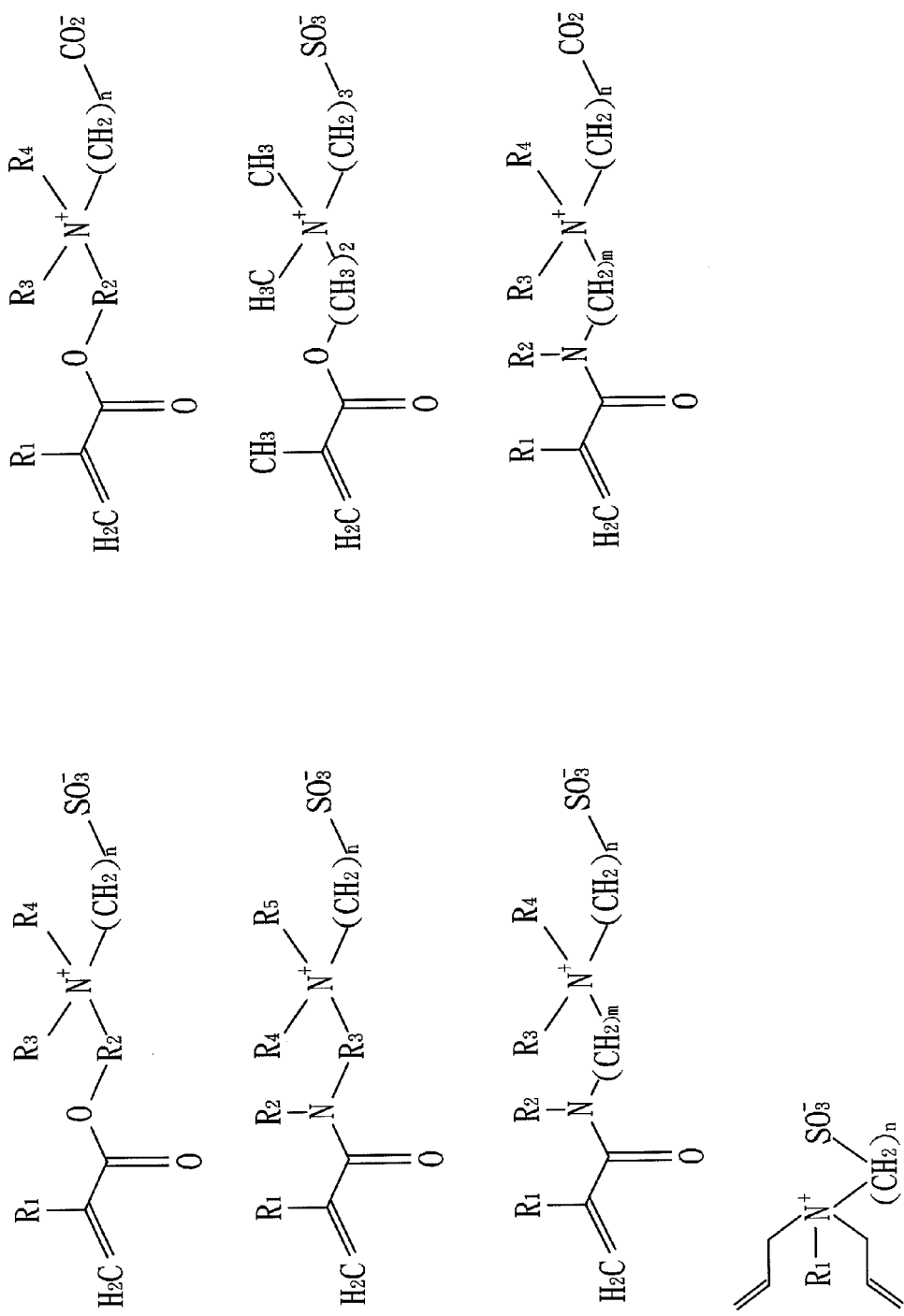
FIGS. 6A, 6B, and 6C respectively show possible chemical structures of the zwitterionic monomer, positively charged monomers, and negatively charged monomers employed by the embodiment to form the zwitterionic block and the anchoring block.
Figure 6B:
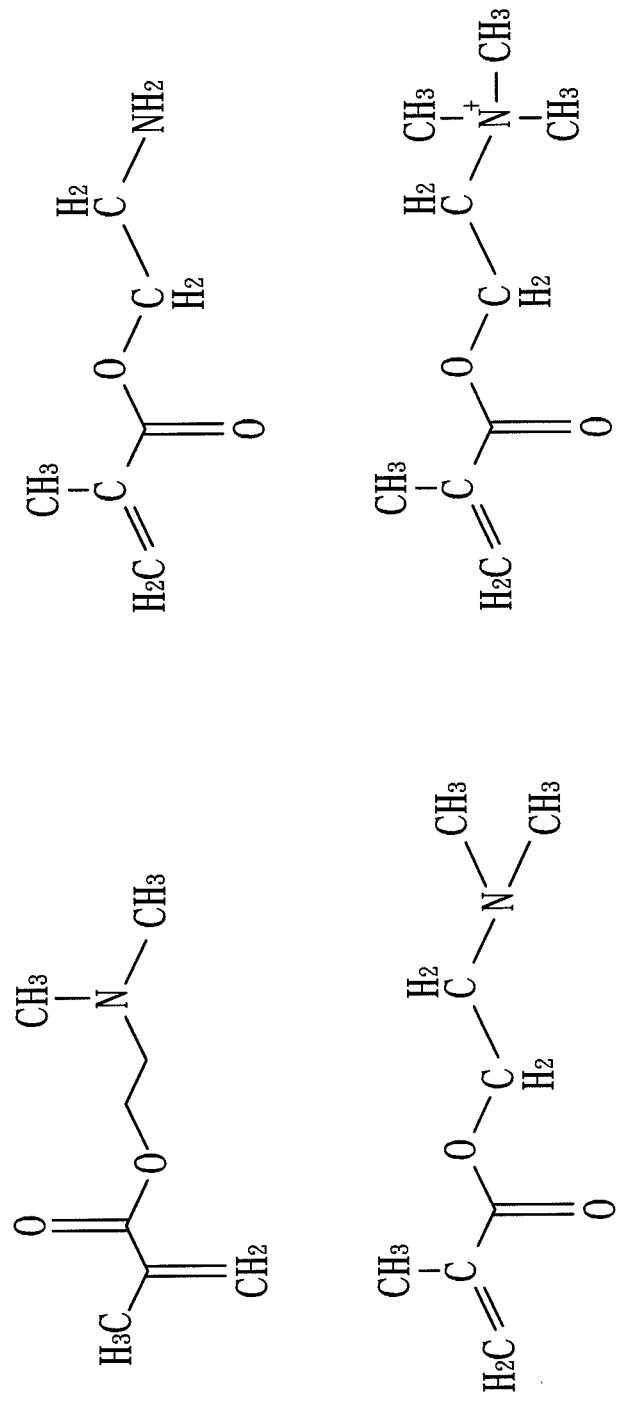
Figure 6C:
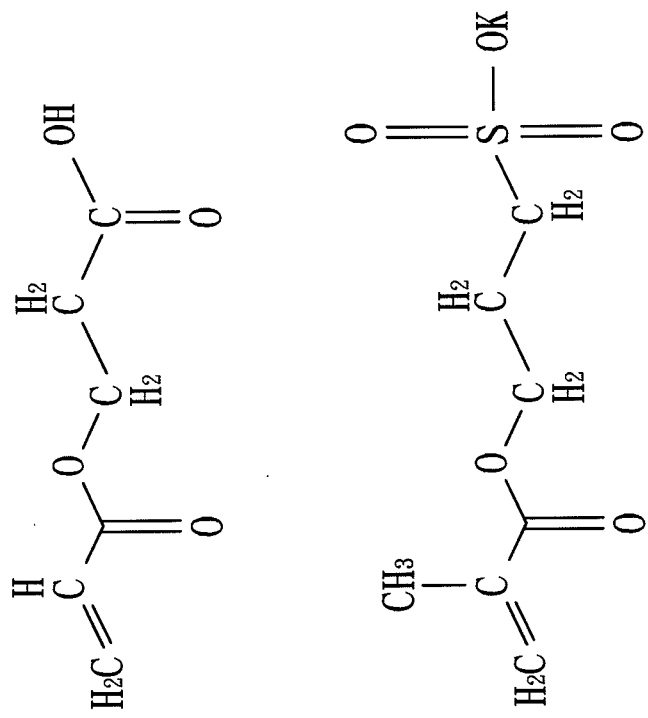

The zwitterionic block could be polymerized by a zwitterionic monomer selected from the group consisting of sulfobetaine, carboxylbetaine, derivatives thereof, and combinations thereof. Furthermore, the zwitterionic block could be polymerized by a zwitterionic unit comprising mix-charged monomers, the mix-charged monomers comprise mixing two oppositely charged compounds with overall charge neutrality. FIGS. 6A, 6B, and 6C respectively show possible chemical structures of the zwitterionic monomer, positively charged monomers, and negatively charged monomers employed by the embodiment to form the zwitterionic block and the anchoring block, where $R_1$-$R_5$ denote alkyl group, m and n are integers of 2 to 5.

The second embodiment of the present invention discloses a method for delivery of a bioactive substance near/into a target cell. First, a bioactive substance-loaded core is provided with a first electricity, wherein the core is embedded with a bioactive substance; Second, one or more block copolymer are provided, each block copolymer comprising a zwitterionic block and an anchoring block with an initial electricity opposite to the first electricity, wherein the anchoring block binds to the core by electrostatic attraction, the zwitterionic block extends outwardly, and a plurality of biocarriers are then self-assembled; Thirdly, the biocarriers are injected into mammalian blood, wherein the biocarriers are circulated to a specific region near the target cell; Finally, an adjusting process to adjust the electricity of the anchoring block, so as to break the binding between the anchoring block and the core, the biocarrier is then disassembled to release the bioactive substance.

The choices of above-mentioned bioactive substance, core, and zwitterionic block are described in the first embodiment.

Figure 5:
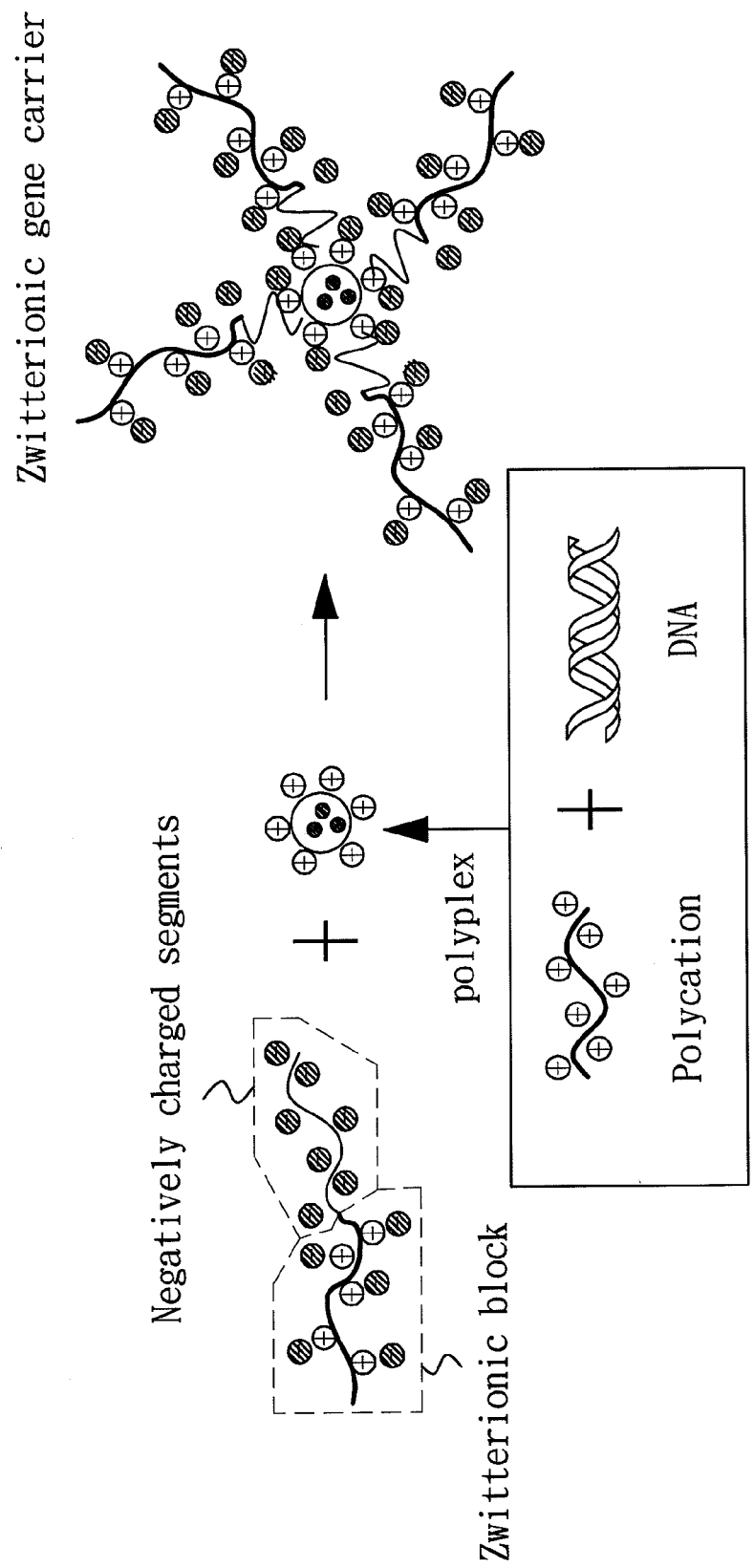
FIG. 5 illustrates a method for forming a gene biocarrier according to an embodiment of the present invention.

In one example of the present embodiment, referring to FIG. 5, the bioactive substance is DNA, interacted with oppositely charged polycation (core), to form a nanometric size polyplex to encapsulate the DNA. Moreover, each block copolymer includes a zwitterionic block and a negatively charged segment (anchoring block). Then the negatively charged segments bind to the positively charged polycation by electrostatic attraction and self-assemble to form a gene biocarrier.

In practical use, after the biocarriers are injected into mammalian blood, the biocarriers are circulated with highly stable structure to a specific region near the target cell. On the other hand, it is also an important issue to take apart/disassemble the biocarrier, so as to release the bioactive substance near or into the target cell.

To fulfill the purpose of taking apart/disassembling the biocarrier, above-mentioned adjusting process is performed to adjust the electricity of the anchoring block, so as to break the binding between the anchoring block and the core, the biocarrier is then disassembled to release the bioactive substance.

Figure 9A:
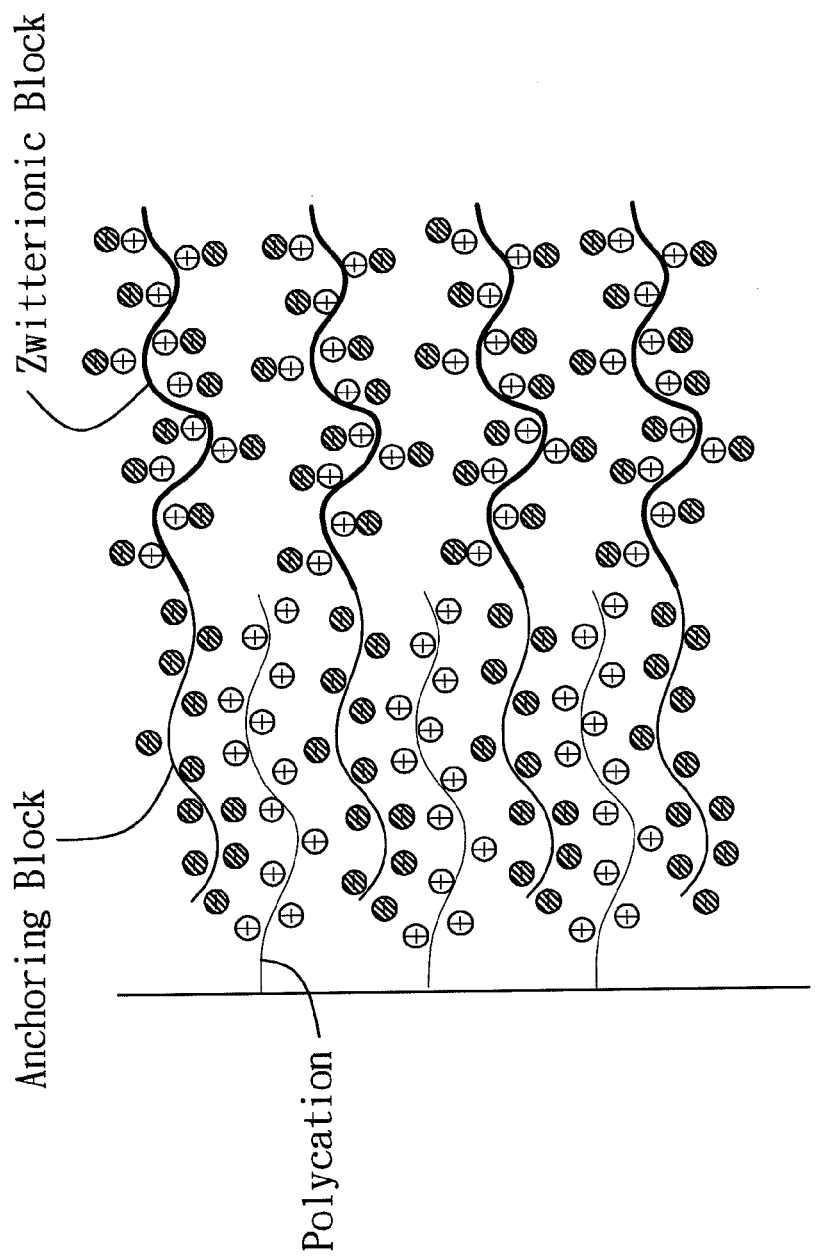
FIG. 9A illustrate a plasmid DNA with polycation surface ligand shielded with the block copolymers.

Because the anchoring mechanism between the block copolymer and the polyplex is very difficult to directly measure in such small scale, a surface grafted with polycation brushes is used as a biomimetic surface of the polyplex surface ligand, as shown in FIG. 9A.

Figure 9B:
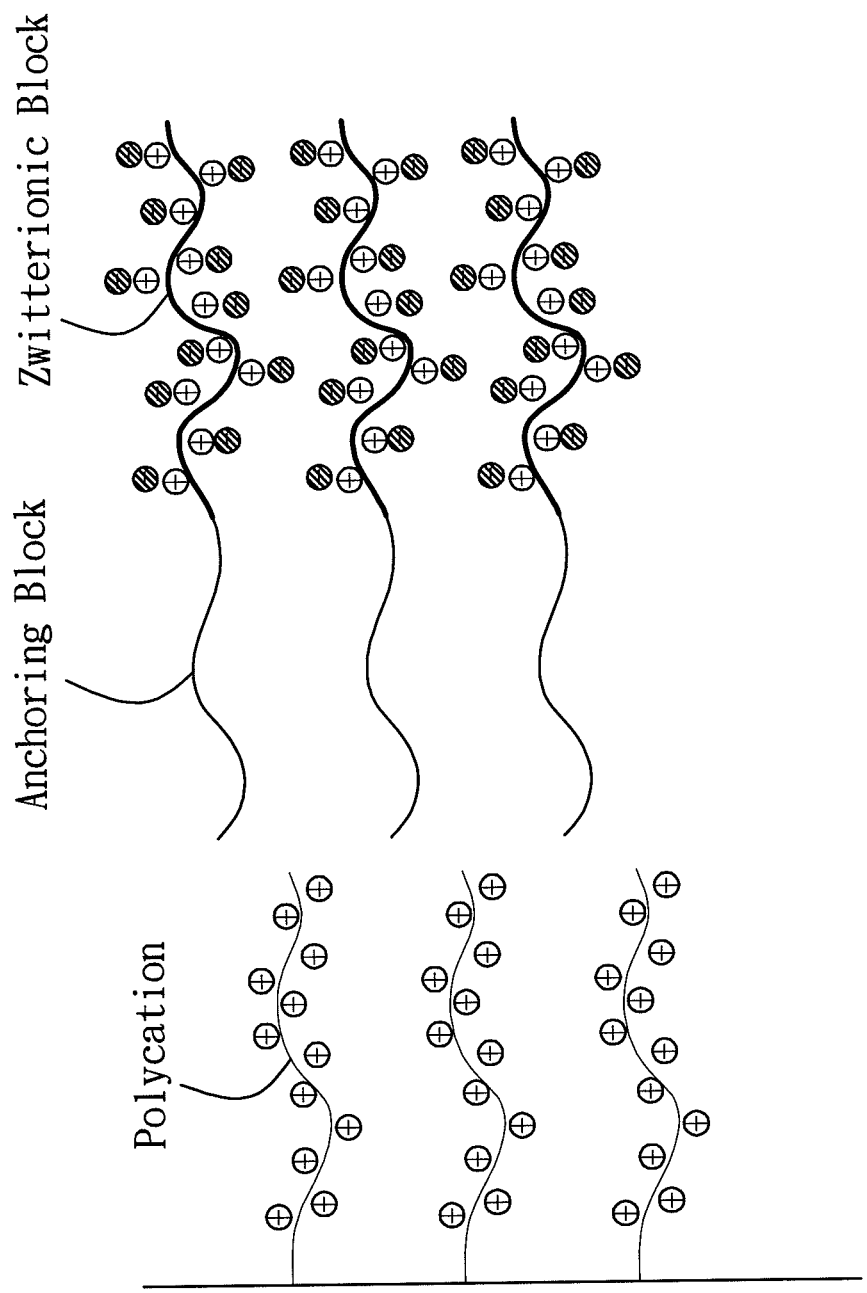
FIGS. 9B-9D illustrate three methods for separating the block copolymers from the polycation block, according to embodiments of the present invention.
Figure 9C:
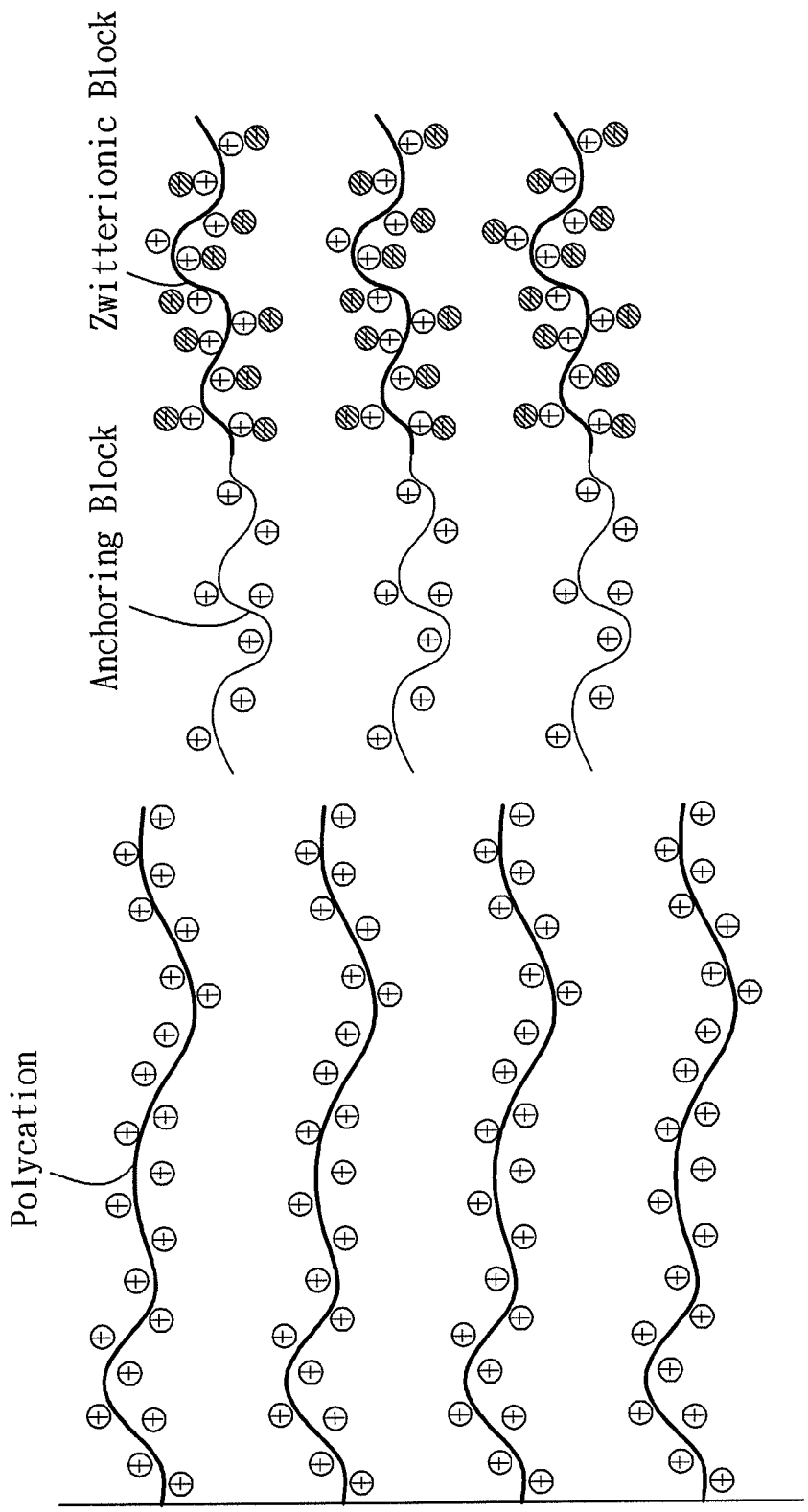
Figure 9D:
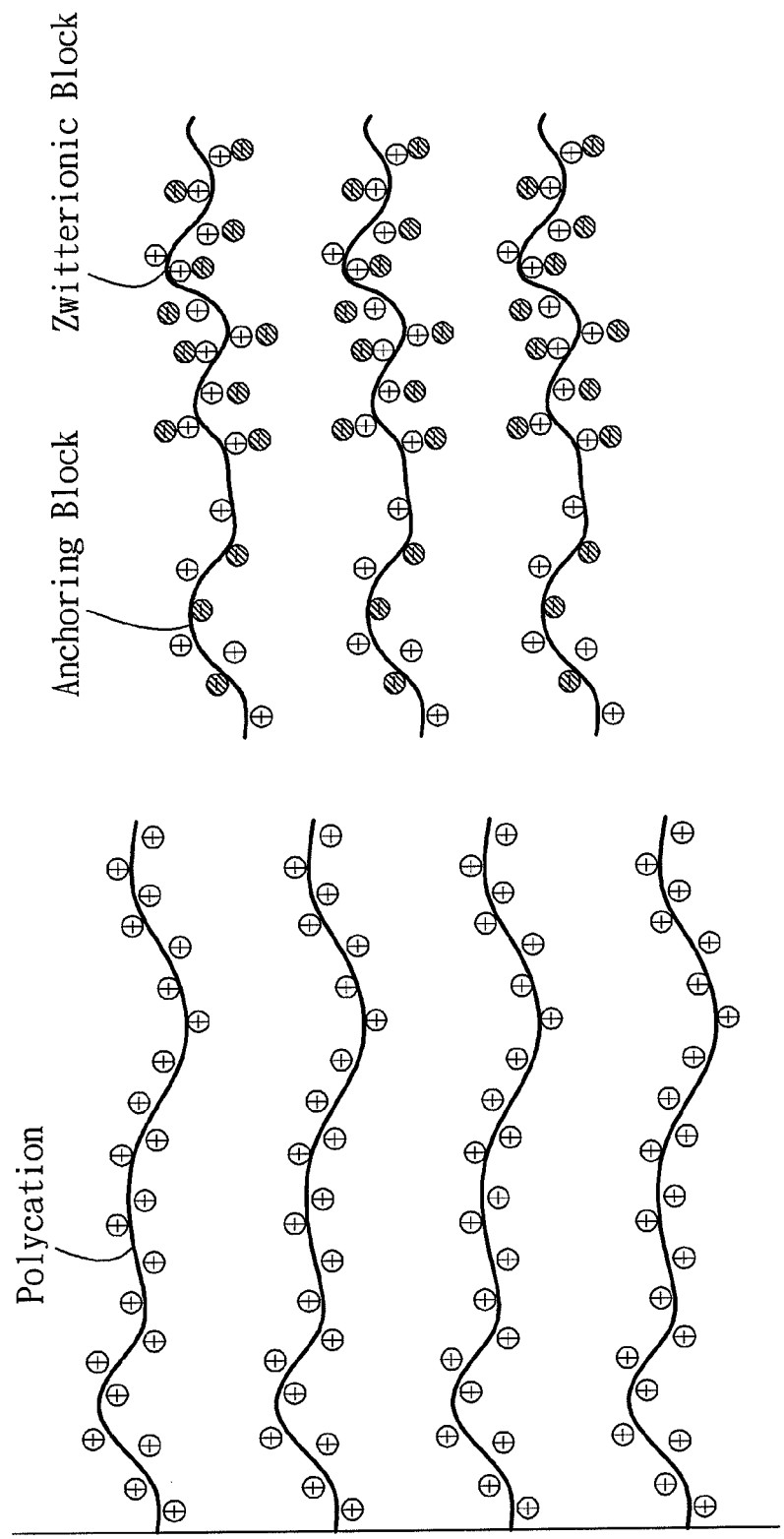

FIGS. 9B, 9C and 9D illustrate 3 proposed ways to break the binding between the anchoring block and the core. Referring to FIG. 9B, the anchoring block with initial electricity (negatively charged) is adjusted to be uncharged, so that electrostatic attraction between the polycation block and the anchoring block disappears and thus the block copolymer can be easily separated. Referring to FIG. 9C, the anchoring block with initial electricity (negatively charged) is adjusted to be positively charged (by generating more positively charged groups), so as to break the binding between the anchoring block and the core by electric repulsion. Referring to FIG. 9D, the anchoring block with initial electricity (negatively charged) is adjusted to be neutrally charged (by generating positively charged groups with the same number as the original negatively charged groups), so that electrostatic attraction between the polycation block and the anchoring block dramatically decreased.

The above three proposed ways may be achieved by adjusting pH value or temperature around the specific region near the target cell. In some embodiment, pH is adjusted to below 7.4 or 6.8. Method of pH adjustment may comprise injection of an agent within the specific region near the target cell.

Method of temperature adjustment may comprise emitting laser at the specific region near the target cell.

Requirement of Block Copolymer and Anchoring Block (Molecular Weight and Relative Block Length)

As mentioned above, because the anchoring mechanism between the block copolymer and the polyplex is very difficult to directly measure in such small scale, a surface grafted with polycation brushes is used as a biomimetic surface of the ployplex surface ligand, as shown in FIG. 9A.

Table 1 lists characteristics of nine prepared diblock copolymers of poly(11-mercaptoundecyl sulfonic acid)-block-poly(sulfobetaine methacrylate) (PSA-b-PSBMA) with variant repeated units of the zwitterionic block (PSBMA) and the anchoring block (PSA), according to an embodiment of the present invention. The nine copolymers were synthesized, but not limited, using atom transfer radical polymerization (ATRP) and varying PSA or PSBMA lengths. Additionally, a surface grafted with polycation brushes of poly(11-mercapto-N,N,N-trimethylammonium chloride) (PTMA) is used as a biomimetic surface of the polyplex surface ligand.

TABLE 1

| Sample ID | Characterization of copolymers $M_w$ (g/mol) | $M_w/M_n$ | Average number of repeated units m | n | Zeta potential $\phi$(mV) | Hydrodynamic size $D_H$(nm) |
|---|---|---|---|---|---|---|
| $PSA_{10}$-b-$PSBMA_{10}$ | 4852 | 1.24 | 11 | 8 | −0.9 | ~11 |
| $PSA_{20}$-b-$PSBMA_{10}$ | 7894 | 1.20 | 23 | 8 | −1.4 | ~12 |
| $PSA_{40}$-b-$PSBMA_{10}$ | 13418 | 1.35 | 46 | 8 | −4.3 | ~12 |
| $PSA_{10}$-b-$PSBMA_{20}$ | 10274 | 1.51 | 13 | 25 | −1.2 | ~12 |
| $PSA_{20}$-b-$PSBMA_{20}$ | 11552 | 1.34 | 19 | 25 | −2.6 | ~11 |
| $PSA_{40}$-b-$PSBMA_{20}$ | 17128 | 1.20 | 41 | 25 | −5.7 | ~11 |
| $PSA_{10}$-b-$PSBMA_{40}$ | 14992 | 1.74 | 12 | 43 | −1.8 | ~12 |
| $PSA_{20}$-b-$PSBMA_{40}$ | 18056 | 1.28 | 24 | 43 | −2.7 | ~13 |
| $PSA_{40}$-b-$PSBMA_{40}$ | 22956 | 1.56 | 44 | 43 | −5.8 | ~14 |

Figure 7:
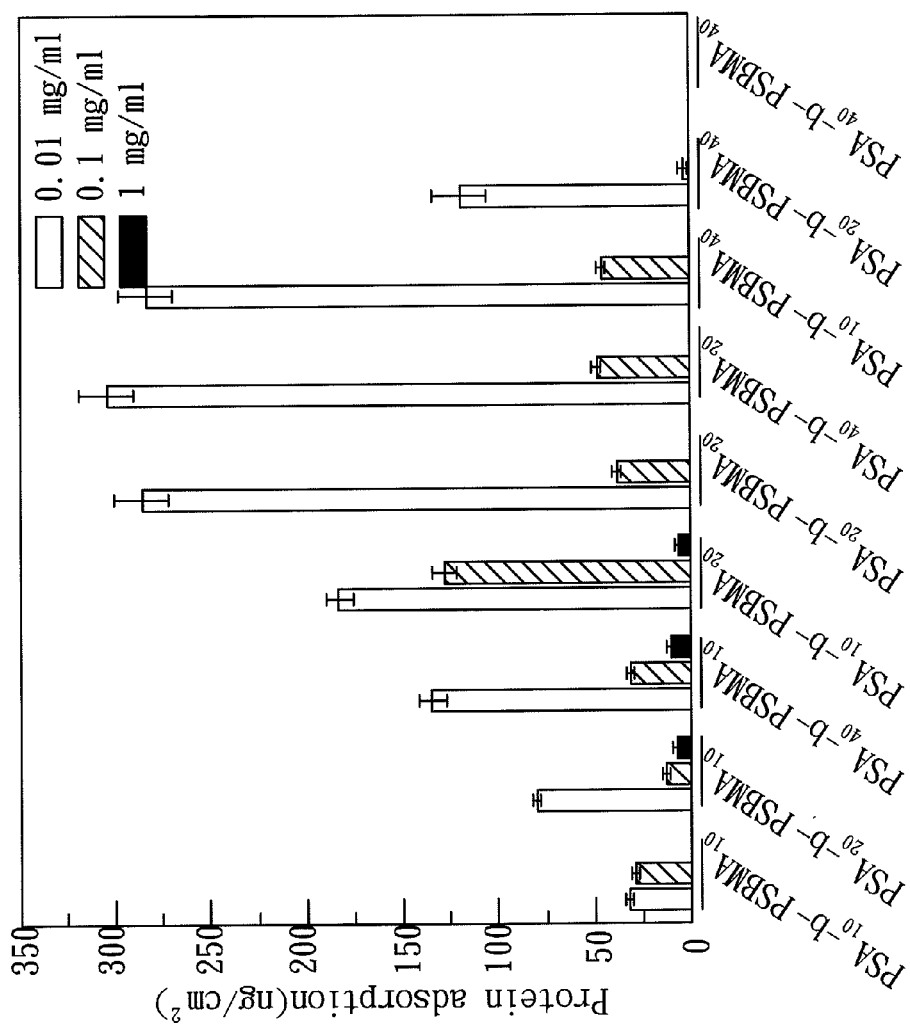
FIG. 7 shows the non-specific protein adsorption of prepared biocarriers shielded by nine copolymers listed in Table 2 with variant concentration in PBS at 23° C.

FIG. 7 shows the non-specific protein adsorption of prepared biocarriers shielded by nine copolymers listed in Table 1 with variant concentration in PBS at 23° C. The protein adsorption is evaluated by SPR method. With concentration 1 mg/ml in PBS, sample $PSA_{10}$-b-$PSBMA_{10}$ $PSA_{40}$-b-$PSBMA_{20}$, $PSA_{10}$-b-$PSBMA_{40}$, $PSA_{20}$-b-$PSBMA_{40}$, and $PSA_{40}$-b-$PSBMA_{40}$ adsorb none of protein. When concentration is decreased to 0.1 mg/ml in PBS, sample $PSA_{20}$-b-$PSBMA_{40}$ and $PSA_{40}$-b-$PSBMA_{40}$ adsorb none of protein. When concentration is decreased to 0.01 mg/ml in PBS, only sample $PSA_{40}$-b-$PSBMA_{40}$ is free of protein adsorption. The results show that the molecular weight ratio of the PSA to PSBMA play an important role in providing resistance to nonspecific protein adsorption. Correct ratios can provide resistance to protein adsorption, wrong ratios cannot.

Figure 8:
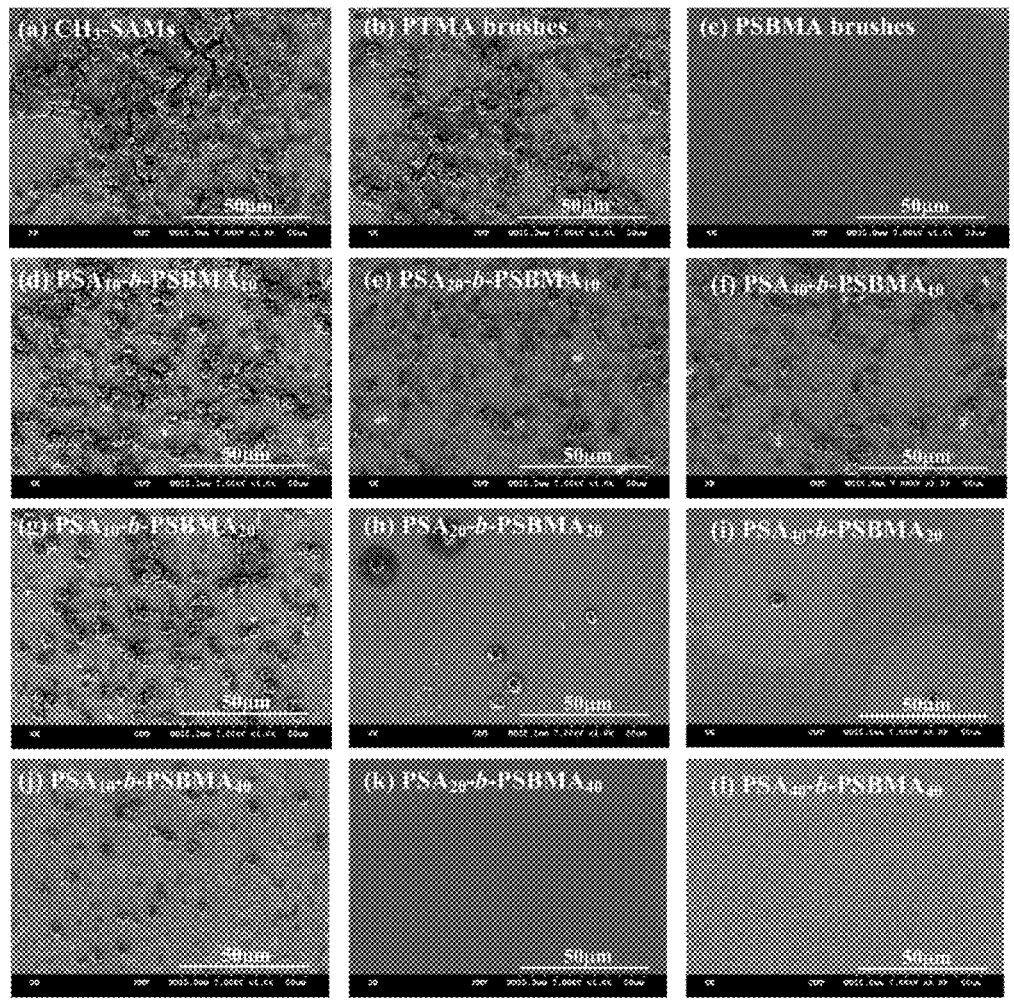
FIG. 8 shows images of platelet adhesion measurements on three comparative samples and the biomimetic surface grafted with copolymers listed in Table 2.

FIG. 8 shows images of platelet adhesion measurements on three comparative samples and the biomimetic surface grafted with copolymers listed in Table 1. The samples are contacted with rich plasma solution platelet activation to investigate its platelet activity. The images indicate that only sample (k) $PSA_{20}$-b-$PSBMA_{40}$ and (l) $PSA_{40}$-b-$PSBMA_{40}$ reveal free of platelet adhesion, same as sample (c) PSBMA brushes. Sample (a) $CH_3$-SAM and sample (b) polyTMA brush lead to serious platelet adhesion. This indicates that polyplex without zwitterionic copolymer shield, or with hydrophobic polymer shield, may induce serious platelet adhesion. In addition, the platelet activation depends on the zwitterionic molar mass ratios of PSA-b-PSBMA. The increase of both ionic SA units and zwitterionic SBMA units in the copolymers tends to effectively reduce the activation of platelets, even to a level of non-platelet adhesion. According to the results, the preferred weight average molecular weight (Mw) of the block copolymer is more than 18 kDa.

Requirement of Block Copolymer and Anchoring Block (Number of Attached Block Copolymers)

A set of zwitterionic polySBMA polymers with varying molecular weights and similar molecular-weight distributions were prepared. A total solids content of 15 wt. % for the different molar ratios of SBMA monomer ([2-(methacryloyloxy)ethyl]dimethyl(3-sulfopropyl)-ammonium hydroxide, sulfobetaine methacrylate) and ammonium persulfate (APS) initiator (See Table 2) was dissolved in 15 mL of deionized water, and nitrogen was bubbled through to remove residual oxygen. The reaction was stirred under positive nitrogen pressure for 6 h at 70° C. After polymerization, the resulting reaction solution was cooled to 4° C. for 3 h and then added slowly into ethanol and redissolved into deionized water repeatedly to precipitate the polymer out of the reaction solution and to remove residual reagents. The copolymer was dried in a freeze dryer at −45° C. to yield a white powder.

TABLE 2

| sample ID | molar ratios[a] [SBMA]/[APS] | characterization of polymers $M_w$ (g/mol)[b] | $M_w/M_n$ | Hydrodynamic size(nm)[c] | critical solution temperature UCST(° C.)[d] |
|---|---|---|---|---|---|
| S250 | 250/1 | 56,608 | 1.85 | ~12 | 28 |
| S350 | 350/1 | 81,633 | 2.00 | ~13 | 30 |
| S450 | 450/1 | 106,841 | 1.93 | ~15 | 33 |
| S550 | 550/1 | 135,849 | 1.62 | ~19 | 35 |
| S750 | 750/1 | 179,955 | 2.02 | ~20 | 43 |
| S1000 | 1000/1 | 256,279 | 1.93 | ~23 | 50 |
| S1250 | 1250/1 | 306,625 | 1.86 | ~21 | 52 |

[a]Reaction molar ratios of SBMA monomer and APS initiator used with fixed total solid content of 15 wt % in the prepared reaction solution.
[b]Weight—average molecular weights ($M_w$) and molecular weight distributions ($M_w/M_n$) were estimated by GPC and calibrated with PEO.
[c]Hydrodynamic diameter of suspended polySBMA polymers in water at 70° C. were estimated by dynamic light scattering.
[d]UCST was determined by reading the absorbance at 550 nm on a UV-Visible spectrophotometer.

The structure of polySBMA polymers was characterized by their $^1$H NMR spectra. The molecular weights of the prepared zwitterionic polymers were determined by aqueous gel-permeation chromatography (GPC) method. The hydrodynamic diameter of the polymers in aqueous solution was estimated by dynamic light scattering (DLS).

Figure 1:
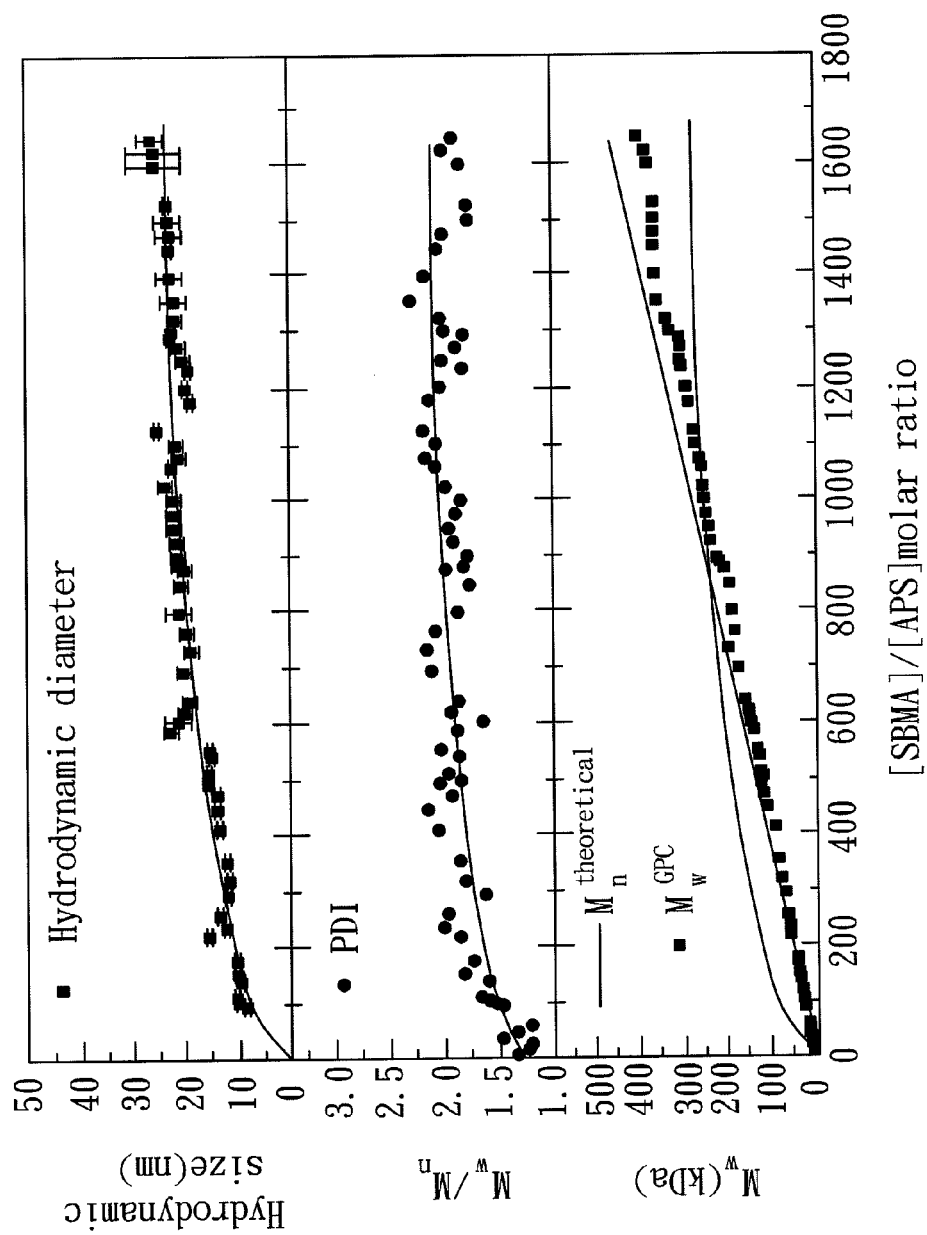
FIG. 1 shows the integrated data of 65 prepared nonfouling polymer samples of an embodiment.

FIG. 1 shows the integrated data of 65 prepared polymer samples of the embodiment. The data includes molecular weights ($M_w$), molecular-weight distribution ($M_w/M_n$), and hydrodynamic size of polySBMA polymers versus molar ratio of SBMA monomer to APS initiator. These results show that controllable molecular weights were obtained for the polySBMA polymers over a wide range, from 1.6 kDa to 450 kDa. Increasing the ratio of SBMA monomer to APS initiator in the reaction solution increase the molecular weight and hydrodynamic size of the prepared zwitterionic polymers. Table 2 lists the characteristic data of seven prepared samples with different molecular weights denoted by S250, S350, S450, S550, S750, S1000, and S1250. The polymer samples have similar molecular-weight distributions (i.e., Mw/Mn=1.8±0.2). Table 3 lists the characteristic data of further ten prepared samples with different molecular weights.

TABLE 3

| sample ID | reaction molar ratios[a] [SBMA]/[APS] | characterization of polymers | | | critical solution temperature UCST(° C.)[d] |
|---|---|---|---|---|---|
| | | $M_w$ (g/mol)[b] | $M_w/M_n$ | Hydrodynamic size(nm)[c] | |
| 5000 | 24/1 | 5,826 | 1.14 | ~5 | 26 |
| 10000 | 38/1 | 10,941 | 1.02 | ~7 | 26 |
| 15000 | 58/1 | 15,280 | 1.41 | ~8 | 29 |
| 23000 | 89/1 | 23,490 | 1.52 | ~8 | non |
| 25000 | 92/1 | 25,365 | 1.31 | 8.14 | non |
| 37000 | 135/1 | 37,267 | 1.62 | 9.82 | 25 |
| 60000 | 210/1 | 62,996 | 1.32 | 16.03 | 32 |
| 120000 | 450/1 | 124,579 | 1.58 | 15.12 | 38 |
| 210000 | 750/1 | 219,603 | 1.76 | 21.46 | 44 |
| 300000 | 1100/1 | 324,521 | 1.82 | 22.31 | 62 |

[a]Reaction molar ratios of SBMA monomer and APS initiator used with fixed total solid content of 15 wt % in the prepared reaction solution.
[b]Weight—average molecular weights ($M_w$) and molecular weight distributions ($M_w/M_n$) were estimated by GPC and calibrated with PEO.
[c]Hydrodynamic diameter of suspended polySBMA polymers in water at 70° C. were estimated by dynamic light scattering.
[d]UCST was determined by reading the absorbance at 550 nm on a UV-Visible spectrophotometer.

Figure 2A:
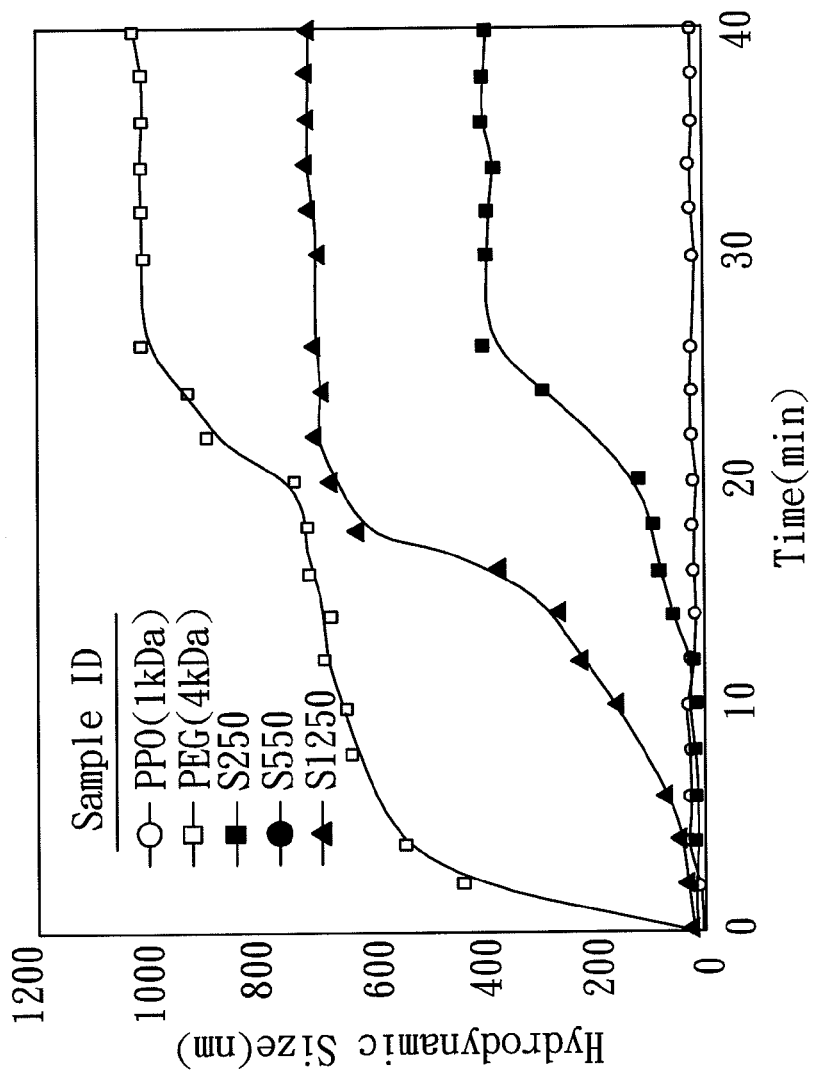
FIGS. 2A and 2B respectively show the hydrodynamic size of prepared polySBMA polymers and comparative samples after contact with 1.0 mg/mL human fibrinogen solution and 100% blood plasma.
Figure 2B:
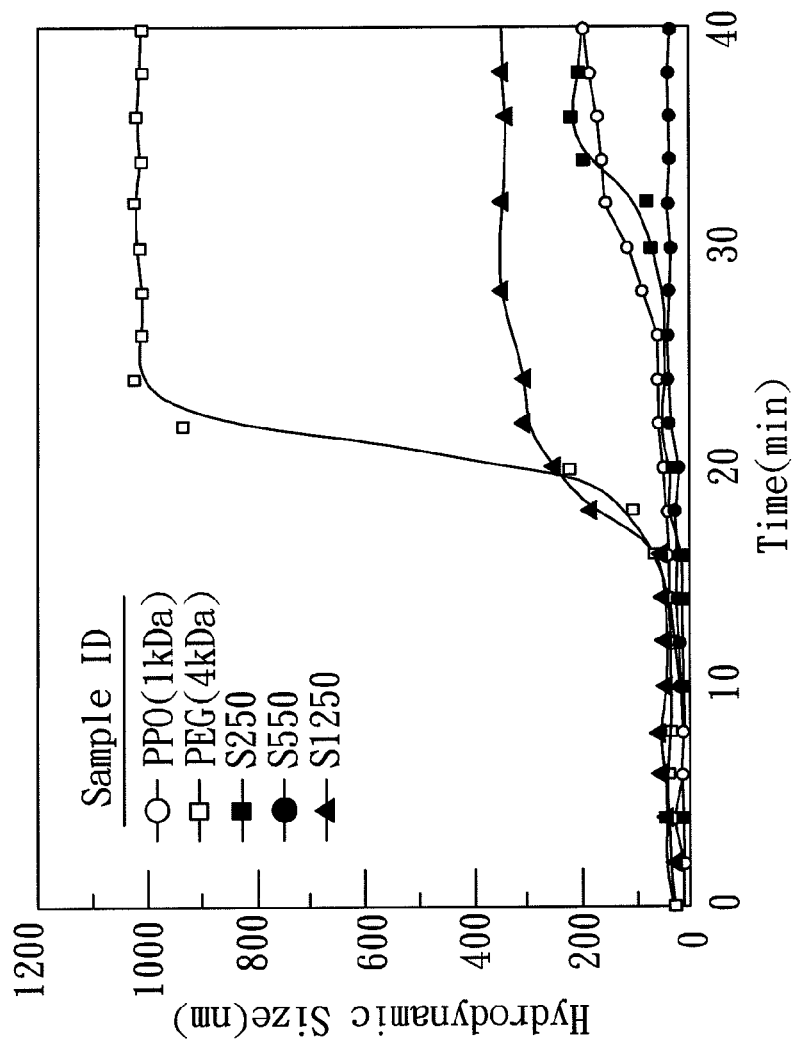

FIGS. 2A and 2B respectively show the hydrodynamic size of prepared polySBMA polymers and comparative samples after contact with 1.0 mg/mL human fibrinogen solution and 100% blood plasma.

In each experiment, a single-protein solution of 1.0 mg/mL human fibrinogen in phosphate buffer saline (PBS, 0.15 M, pH 7.4) was prepared at 37° C., a platelet-poor plasma (PPP, 100% blood plasma) solution was prepared by centrifugation of human blood at 3,000 rpm for 10 min at 37° C., and a volume of 100 µL of the fibrinogen solution (1.0 mg/mL) or PPP solution (100%) was mixed with 100 µL of polymer solution (10 mg/mL) at 37° C.

As shown in FIG. 2A, after mixture with single-protein fibrinogen in PBS solution, the hydrodynamic diameter of protein-adsorbed PPO particles increased to ~1,000 nm after 25 min, indicating a dramatic aggregation due to the hydrophobic interaction between PPO and protein. As expected, the PPO polymer, presenting hydrophobic methyl groups, induced large amounts of protein adsorption. Similar to the stability of PEG in the fibrinogen solution, the hydrodynamic diameter of the polymer S550 remained nearly constant at 16.7±0.2 nm, with no obvious size increase during the test period of 40 min. This indicates that polymer S550 is quite stable in the presence of a single-protein solution under physiological conditions.

As shown in FIG. 2B, the PPO polymer with hydrophobic methyl groups induced nonspecific protein adsorption in plasma due to hydrophobic interactions. The hydrodynamic diameter increments of PEG, S250, and polymer S1250 were about 200 nm, 200 nm, and 300 nm, respectively, after an incubation period of 40 min. Surprisingly, polymer S550 exhibited almost the same hydrodynamic size without nonspecific protein adsorption in 100% plasma, indicating its excellent nonfouling stability. Notice that the adsorption of components from PPP solution onto the dispersed polymer surface occurs not only with the major protein components of plasma but also other small biomolecules such as amino acids, lipids, urea, fats, and polysaccharides. The above results demonstrate that the nonspecific protein-adsorption characteristics of polySBMA polymers are strongly associated with their molecular weights in single-protein solution or 100% plasma under physiological conditions.

Anticoagulant Activity of polySBMA Polymers in Human Plasma Solution

In general, nonspecifically adsorbed plasma proteins interact in a serious of reactions leading to plasma clotting. Among plasma proteins, fibrinogen plays a leading role in mediating surface-induced activation as polymeric materials contact human blood plasma under static conditions. The measurement of plasma clotting time has already become a recognized test to estimate the blood compatibility of a prepared material.

Figure 3A:
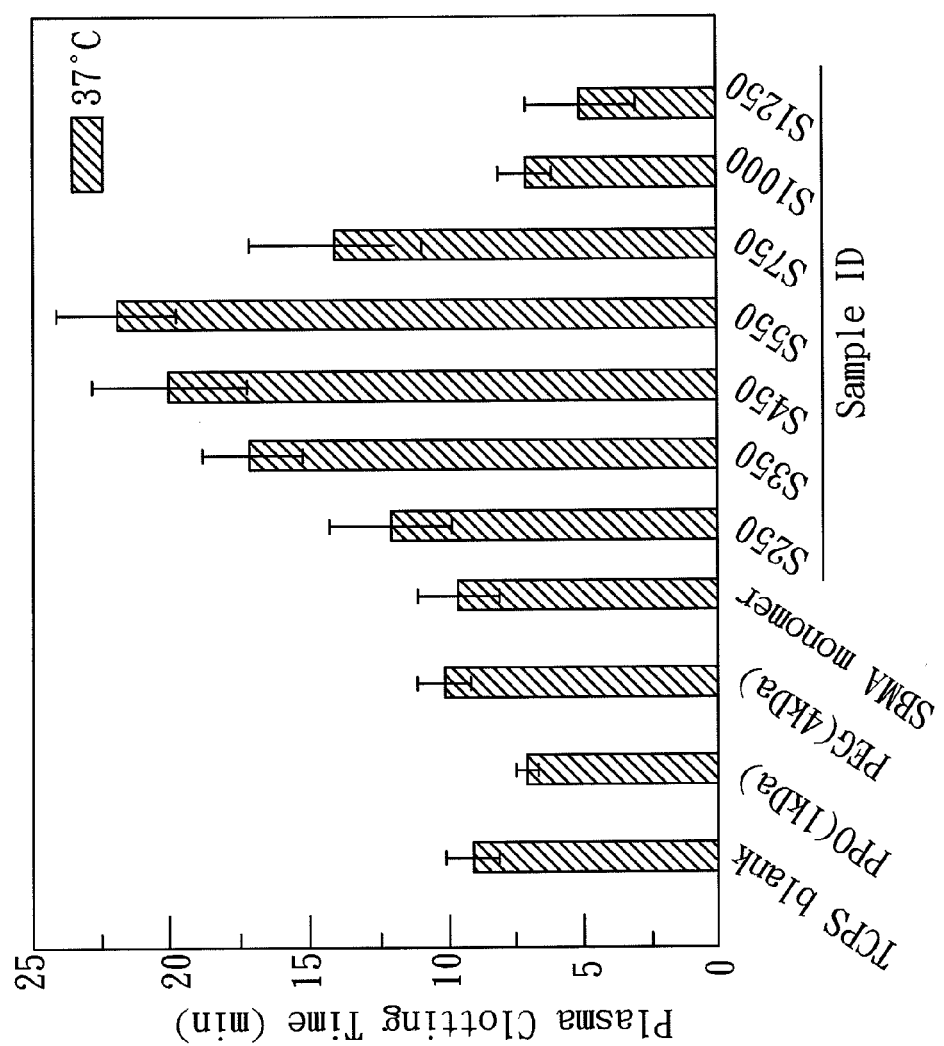
FIGS. 3A and 3B show the plasma-clotting time of recalcified platelet-poor plasma in the presence of prepared polymers.
Figure 3B:
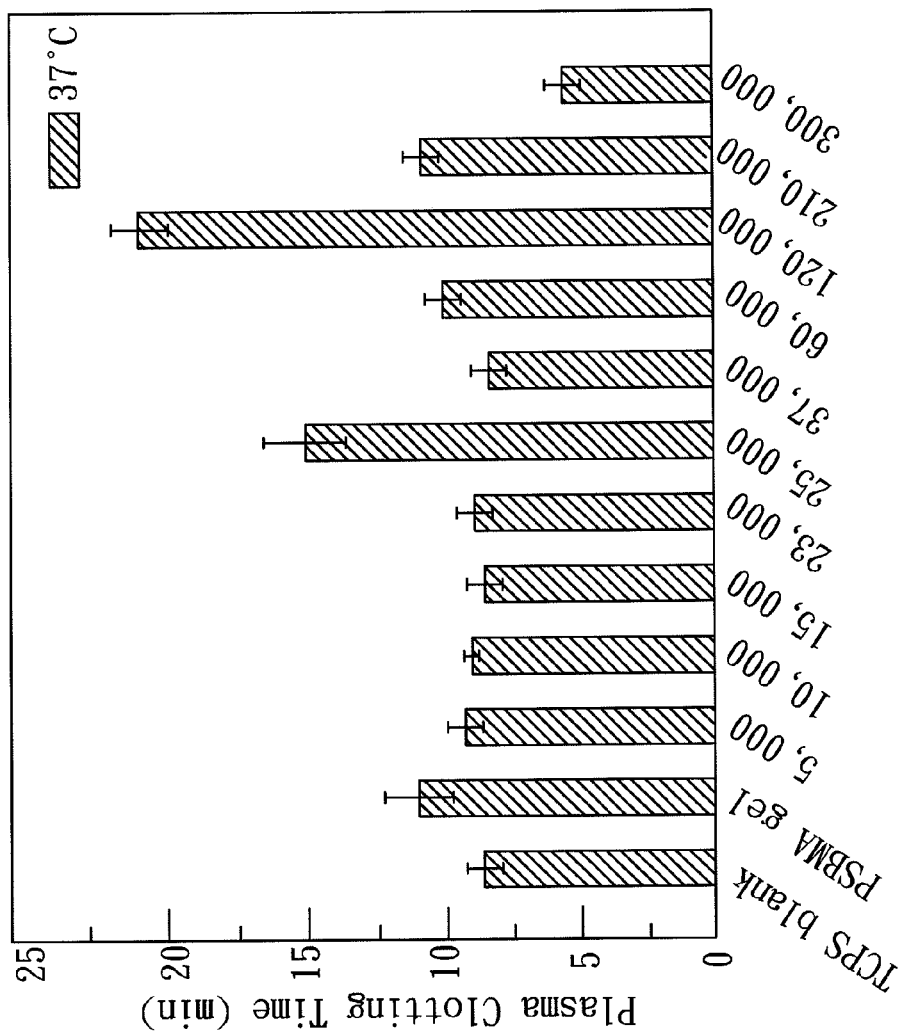

FIGS. 3A and 3B show the plasma-clotting time of recalcified platelet-poor plasma in the presence of prepared polymers, where FIG. 3A shows data of polySBMAs listed in Table 2, and FIG. 3B shows data of polySBMAs listed in Table 3. Clotting time for blank PS wells was 9±1.0 min at 37° C. Each clotting time is an average value of six samples. The prepared polySBMA samples with molecular weight S250, S350, S450, S550, S750, S1000, S1250, 5000, 10000, 15000, 23000, 25000, 37000, 60000, 120000, 210000, 300000, and commercial PPO (molecular weight 1 kDa) and PEG (molecular weight 4.2 kDa, polydispersity 1.1) at 10 mg/mL were added to recalcified human PPP solution in a PS 96-well plate at physiologic temperature of 37° C.

When the hydrophobic PPO (1 kD) was put into the recalcified PPP solution, the clotting time decreased to ~7 min. The result indicates that hydrophobic PPO is a highly activating polymer activating plasma clotting through the intrinsic coagulation pathway. Almost no change in plasma clotting time of the absence or presence of PEG was observed. The results indicate that PEG polymers do not activate plasma clotting. Similar to PEG, SBMA monomer did not activate plasma clotting and exhibited no anticoagulant activities at 37° C.; polySBMA gel can slightly prolong the plasma-clotting time. When polymer S250 was added into PPP solution, the average clotting time increased to ~12 min, indicating an anticoagulant activity of polySBMA. The plasma-clotting time of sample with molecular weight 25,000 was prolonged to ~15 min. In the case of polymer S550 or sample with molecular weight 120,000, the plasma-clotting time was further prolonged to ~20 min at 37° C. Plasma-clotting time as well as anticoagulant activity was maximized when the molecular weight of polySBMA was about 130 kDa. Above this molecular weight, plasma clotting time decreased as the polymer molecular weight increased.

In physiological conditions at 37° C., the plasma-clotting time for S550 was much higher than that for blank PS wells, while the SBMA monomer exhibited no anticoagulant activity and S1250 lost its anticoagulant activity in 100% plasma. The polySBMA with an $M_w$ of about 130 kDa presented the best anticoagulant activity in 100% blood plasma, which is due to the fact that the S550 polymer is highly stable and resistant to nonspecific protein adsorption from fibrinogen solution and 100% plasma. This clearly indicates that polySBMA has a molecular-weight dependence with respect to anticoagulant activity or contact activation for preventing or activating plasma clotting in human blood.

Antihemolytic Activity of polySBMA Polymers in RBC Solution

To further evaluate the influence of polymer molecular weights on blood compatibility of prepared polySBMA, a red blood cell (RBC) hemolysis assay was performed. The observed hemolysis of RBCs in DI water and PBS solutions at 37° C. were used as positive and negative controls, respectively. The observed hemolytic activity of polySBMA at a given molecular weight at 37° C. was normalized to that of the positive control, DI water. The hemolytic activity of hydrophobic PPO (1 kD), hydrophilic PEG (4 kD), and heparin were also tested as references for comparison.

Figure 4A:
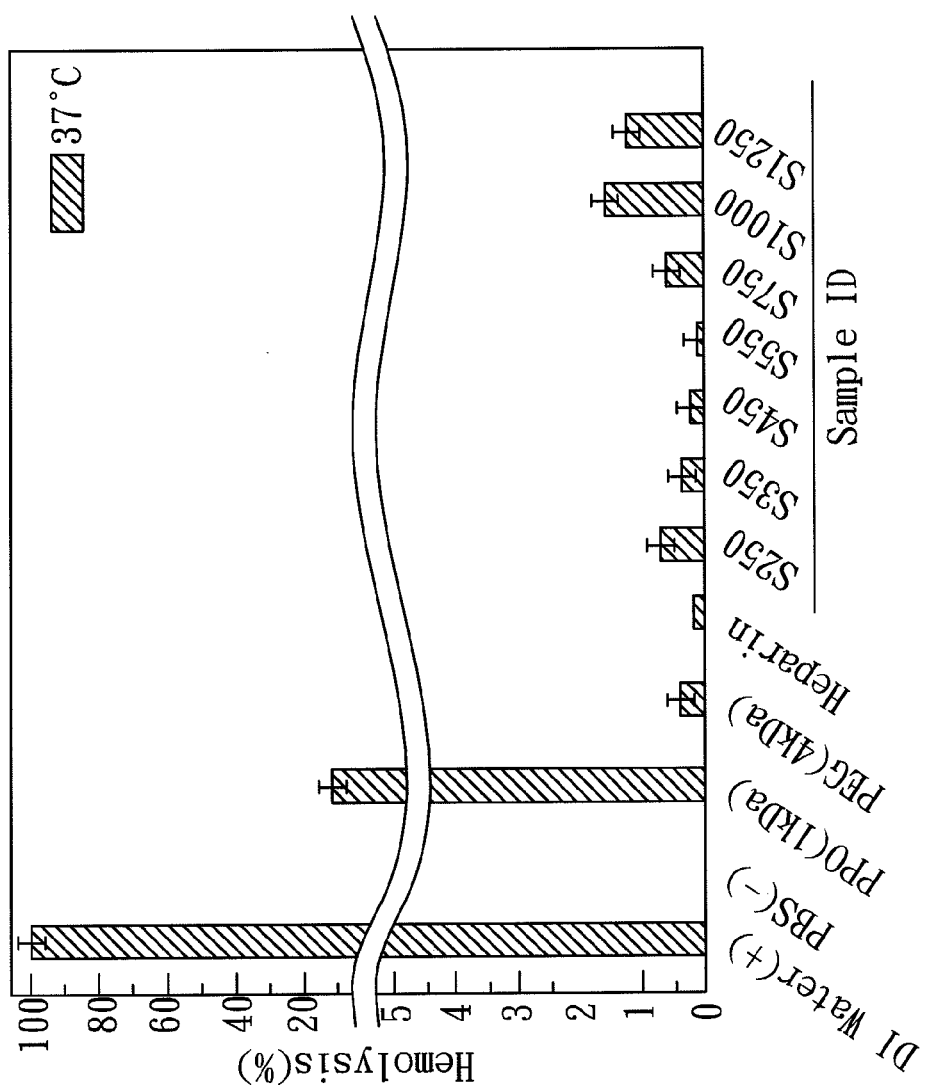
FIGS. 4A and 4B show the molecular weight dependent hemolytic activity of the prepared polySBMA polymers in RBC solution.
Figure 4B:
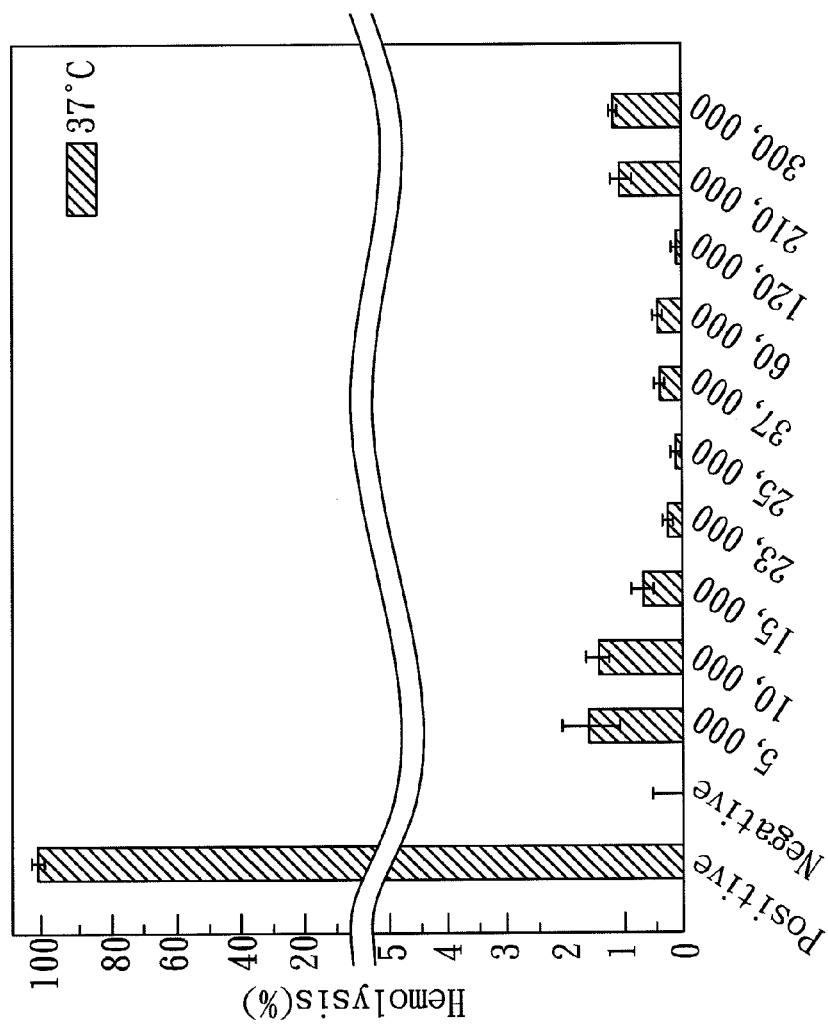

FIGS. 4A and 4B show the molecular weight dependent hemolytic activity of the prepared polySBMA polymers in RBC solution, according to the embodiment of the present invention. In general, hydrophobic polymers are capable of interacting with biological membranes, causing disruption. Thus, it was observed that PPO exhibited ~12% hemolytic activity. No apparent hemolytic activity was observed for the references of PEG and heparin (less than 1%). It is observes that hemolytic activity exhibits minimum at specific molecular weight of about 25 kDa, 120 kDa, and 130 kDa (S550), which are comparable with heparin. However, all of polySBMA in RBC solution at physiologic conditions showed very little hemolysis (less than 2%), indicating good nonfouling nature of zwitterionic polymers with anti-hemolytic activity to resist the disruption of blood cell membranes.

According to the results of FIGS. 4A and 4B again, 2 relatively stable regions of molecular weight exist. One is low molecular weight region (LW), and the other is high molecular weight region (HW). In common cases, one biocarrier usually with 2 or more ligands; therefore, results of FIGS. 4A and 4B indicates LH is suitable for single ligand, and HW is suitable for summation of the Mw of all the ligans.

In one example of this embodiment, the summation of the weight average molecular weight (Mw) of all the block copolymers ranges from 80 kDa to 180 kDa. When Mw of the block copolymer is about 18 kDa, the number of block copolymer ranges from 4 to 10.

Detailed experiment procedure and data are discussed in a disclosure entitled "Tunable Blood Compatibility of Polysulfobetaine from Controllable Molecular-Weight Dependence of Zwitterionic Nonfouling Nature in Aqueous Solution" received by *Langmuir,* 2010, by Yung Chang et al., the disclosure of which is hereby incorporated by reference.

Although specific embodiments have been illustrated and described, it will be appreciated by those skilled in the art that various modifications may be made without departing from the scope of the present invention, which is intended to be limited solely by the appended claims.

What is claimed is:

1. A biocarrier for delivery of a bioactive substance near/into a target cell, comprising:
    a bioactive substance-loaded core with a positive charge, wherein the bioactive substance-loaded core consists of DNA and a polycation; wherein the polycation is formed by incorporation of a monomer selected from the group consisting of following:

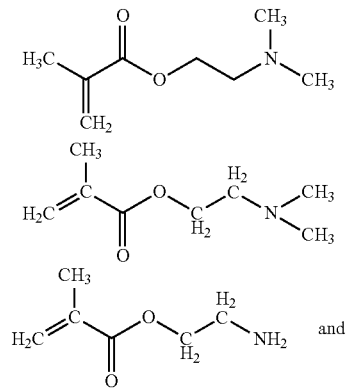

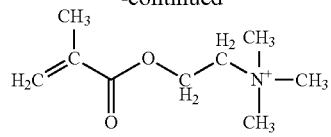

and
    one or more block copolymer, each block copolymer comprises a zwitterionic block and an anchoring block, wherein the anchoring block is with a negative charge, the zwitterionic block is formed by incorporation of a zwitterionic monomer, and the zwitterionic monomer is a sulfobetaine compound;
    wherein the anchoring block binds to the core by electrostatic attraction, and the zwitterionic block extends outwardly to increase the biocarrier stability in mammalian blood.

2. The biocarrier for delivery of a bioactive substance near/into a target cell as recited in claim 1, wherein the sulfobetaine compound is selected from the group consisting of the following:

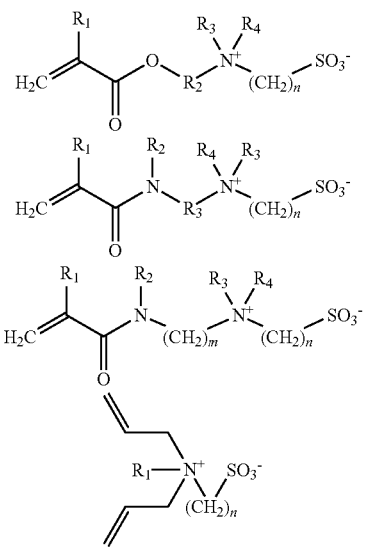

where R1, R2, R3, R4, and R5 are alkyl group; m and n are integers of 2 to 5 and

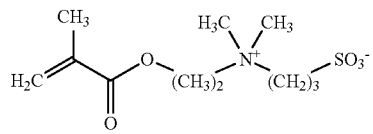

3. The biocarrier for delivery of a bioactive substance near/into a target cell as recited in claim 1, wherein the zwitterionic block is a poly(sulfobetaine methacrylate).

4. The biocarrier for delivery of a bioactive substance near/into a target cell as recited in claim 3, wherein the weight average molecular weight (Mw) of poly(sulfobetaine methacrylate) ranges from 5,000 g/mol to 220,000 g/mol.

5. The biocarrier for delivery of a bioactive substance near/into a target cell as recited in claim 3, wherein the weight average molecular weight (Mw) of poly(sulfobetaine methacrylate) ranges from 100,000 g/mol to 180,000 g/mol.

6. The biocarrier for delivery of a bioactive substance near/into a target cell as recited in claim 3, wherein the weight average molecular weight (Mw) of poly(sulfobetaine methacrylate) being 120,000 g/mol provides a plasma clotting time prolonged to 20 minutes at 37° C.

7. The biocarrier for delivery of a bioactive substance near/into a target cell as recited in claim 3, wherein the weight average molecular weight (Mw) of poly(sulfobetaine methacrylate) ranging from 120,000 g/mol to 180,000 g/mol provides a critical solution temperature at 38° C. to 43° C.

8. The biocarrier for delivery of a bioactive substance near/into a target cell as recited in claim 1, wherein the anchoring block is polymerized by a monomer selected from the group consisting of following:

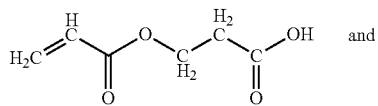 and

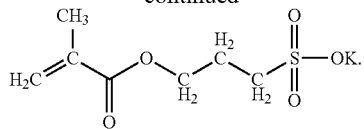

9. The biocarrier for delivery of a bioactive substance near/into a target cell as recited in claim 1, wherein the block copolymer is a diblock copolymer of poly(11-mercaptoundecyl sulfonic acid)-block-poly(sulfobetaine methacrylate).

10. The biocarrier for delivery of a bioactive substance near/into a target cell as recited in claim 9, wherein the diblock copolymer of poly(11-mercaptoundecyl sulfonic acid)-block-poly(sulfobetaine methacrylate) having the weight average molecular weight (Mw) is more than 18 kDa.

11. The biocarrier for delivery of a bioactive substance near/into a target cell as recited in claim 9, wherein the diblock copolymer of poly(11-mercaptoundecyl sulfonic acid)-block-poly(sulfobetaine methacrylate) having the average number of repeated units of poly(11-mercaptoundecyl sulfonic acid) is more than 20 and the average number of repeated units of poly(sulfobetaine methacrylate) is more than 40.

\* \* \* \* \*